(12) United States Patent  
Teufelberger et al.

(10) Patent No.: US 8,715,245 B2
(45) Date of Patent: May 6, 2014

(54) DEVICES AND METHODS FOR INJECTION OF MEDIA INTO HUMAN AND ANIMAL TISSUE

(75) Inventors: Gunter Teufelberger, Bürmoos (AT); Hannes Wagner, Salzburg (AT); Christine Oberascher, Nussdorf (AT); Stefan Kapeller, Nussdorf (AT); Rainer Sigl, Haigermoos (AT); Udo Hoermann, Oberalm (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 993 days.

(21) Appl. No.: 12/178,811

(22) Filed: Jul. 24, 2008

(65) Prior Publication Data

US 2009/0030376 A1     Jan. 29, 2009

(30) Foreign Application Priority Data

Jul. 25, 2007   (EP) .................................. 07014560

(51) Int. Cl.
*A61M 5/00*   (2006.01)
*A61M 31/00*  (2006.01)

(52) U.S. Cl.
USPC .......................................... 604/188; 604/506

(58) Field of Classification Search
USPC ........................ 604/506, 80, 188, 240, 243
See application file for complete search history.

(56) References Cited

U.S. PATENT DOCUMENTS

| | | | |
|---|---|---|---|
| 2,773,500 A | 12/1956 | Young | |
| 3,150,661 A * | 9/1964 | Maki | 604/192 |
| 3,811,442 A | 5/1974 | Maroth | |
| 4,381,777 A * | 5/1983 | Garnier | 604/188 |
| 4,787,893 A | 11/1988 | Villette | |
| 7,670,328 B2 * | 3/2010 | Miller | 604/506 |
| 2006/0106363 A1 * | 5/2006 | Aravena et al. | 604/506 |

FOREIGN PATENT DOCUMENTS

| | | |
|---|---|---|
| DE | 102 54 442 | 6/2004 |
| FR | 2 581 548 | 11/1986 |
| WO | 96/30065 | 10/1996 |
| WO | 96/39213 | 12/1996 |
| WO | 00/09186 | 2/2000 |
| WO | 00/67822 | 11/2000 |
| WO | 01/32241 | 5/2001 |
| WO | 2007/018809 | 2/2007 |

OTHER PUBLICATIONS

European Search Report for EP 07 01 4560 (mailed Mar. 12, 2008).

* cited by examiner

*Primary Examiner* — Kevin C Sirmons
*Assistant Examiner* — William Carpenter
(74) *Attorney, Agent, or Firm* — Klarquist Sparkman, LLP

(57) ABSTRACT

Embodiments of a medical hand-grip element for injection of a substance from an ampoule, comprise a drive device for driving the ampoule and the injection needle, a delivery device for delivering the medicinal substance out of the ampoule and a coupling device for rotationally fixed coupling of the ampoule with the injection needle and for preventing a relative movement between the ampoule and the injection needle is disclosed. Embodiments of injection systems, injection units, injection needles and handling methods for them are also disclosed in which the risk of injury and contamination for the user is reduced by providing approaches for covering the ends of the cannulas of the injection needles during a number of handling steps.

22 Claims, 5 Drawing Sheets

DEVICES AND METHODS FOR INJECTION OF MEDIA INTO HUMAN AND ANIMAL TISSUE

CROSS REFERENCE TO RELATED APPLICATION

The present application claims priority from pending European Patent Application No. 07014560 filed Jul. 25, 2007, which is incorporated herein by reference.

BACKGROUND

1. Field

The present invention relates to devices and methods for injection of media into human and animal tissue, in particular into hard tissue.

2. Description of Prior Art

U.S. Pat. No. 4,787,893 discloses a hand-grip element for injection of liquid substances, in particular anesthetics, in which rotation of a receptacle sleeve is induced by a drive motor. The ampoule with the substance to be injected can be inserted into the receptacle sleeve, so that the rotational movement is transferred to the ampoule and the injection needle connected to it. The hand-grip element is thus used not only for injection but also for penetrating into or through tissue, i.e., bones, for example, in particular the jawbone, into which the substance is to be injected.

The connection of the ampoule to the injection needle is accomplished by puncturing a rubber stopper, the so-called septum, which is provided at one end of the ampoule, so that the injection needle protrudes into the ampoule reservoir with the injection liquid. However, this connection has proven to be a disadvantage because in drilling through the bone, the needle, which serves as the drill, is decelerated but the holding power of the rubber stopper for the needle is too low to transfer the decelerating effect to the ampoule as well, which thus results in a relative movement between the needle and the ampoule. Abrasion occurs on the rubber stopper due to this relative movement, i.e., due to the rubber stopper rotating more rapidly and the decelerated injection needle rotating more slowly. At least some of the abrasion enters the injection liquid in the form of fine rubber particles, so there is the risk that these particles may be injected into the tissue with the injection liquid. More of the abrasion enters the hand-grip element, where it can lead to negative effects or damage to components.

Therefore, the object of the present invention is to design a hand-grip element so that no abrasion occurs.

SUMMARY

According to one embodiment, the medical hand-grip element comprises a coupling arrangement for rotationally fixed coupling or connection of the ampoule to the injection needle. The coupling arrangement, also referred to as "antitwist protection," produces a coupling, preferably mechanical, of the ampoule to the injection needle between the ampoule and the injection needle, so that the ampoule and the injection needle rotate at essentially the same rotational speed, so that a relative movement between the ampoule and the injection needle and thus abrasion of the rubber stopper (septum) of the ampoule are prevented.

In order for the ampoule and the injection needle to rotate at essentially the same rotational speed, a reliable transfer of torque from the drive device of the medical hand-grip element to the ampoule and the injection needle and also a transfer of the resulting braking force, e.g., occurring during the drilling through bone tissue, to the injection needle and the ampoule are necessary. In one embodiment, the coupling arrangement therefore has a coupling device with at least one coupling element which is designed in particular as a spring strap, spring arm, tension surface, thread, entraining element and/or form-fitting element, or is connected to such a coupling device. The at least one coupling element couples the ampoule and/or the injection needle directly or indirectly to the drive device and preferably also to the coupling arrangement, so that essentially the same torque acts on the ampoule, the injection needle and the coupling arrangement.

Another requirement for the drive of the ampoule and the injection needle with essentially the same rotational speed consists of a reliable connection of the ampoule to the injection needle. Therefore, in one embodiment, the coupling arrangement has a connecting member for the ampoule and the injection needle. This joint connecting member can include, for example, a borehole or a hollow shaft into which the injection needle and/or the ampoule can be inserted at least partially or has a protrusion to which the injection needle and/or the ampoule can be connected. The connecting member may of course have a different design.

During operation of the medical hand-grip element, the coupling arrangement, which is preferably provided with the coupling element and the connecting device, as well as the ampoule and the injection needle, thus form a unit on which substantially the same torque acts and which thus rotates at substantially the same rotational speed. In other words, the unit is designed to transfer and/or receive a uniform common torque and a uniform common rotational speed.

According to a especially preferred embodiment, the connecting device of the coupling arrangement is designed as a hollow shaft with one coupling element each for transfer of torque for the ampoule and for the injection needle. This design ensures an especially reliable transfer of torque, stable bearing support and extremely smooth operation of the injection needle and the ampoule.

If the coupling arrangement is designed as a hollow shaft, it then surrounds the ampoule and the injection needle at least partially. The coupling arrangement and/or the connecting device may, however, also be arranged at least partially between the ampoule and the injection needle, e.g., when the connecting device has a thread onto which the injection needle is screwed.

To further support the rotationally fixed connection between the ampoule and the injection needle, in one embodiment it is provided that a chucking element is provided on the coupling arrangement, reinforcing the connection of these two elements. The chucking element is preferably provided on a coupling element or is designed as part thereof so that it is advantageously arranged in the immediate area of torque transfer. The chucking element especially preferably has at least one conical surface on the inside of the hollow shaft which serves as the connecting device. The conical surface is designed so that it presses a part of an injection needle inserted into the hollow shaft, in particular a section of the needle apron, against the ampoule. This chucking device which is formed by parts of the injection needle and the chucking element in the hollow shaft represents a very simple and effective reinforcement of the rotationally fixed connection between the ampoule and the injection needle.

The drive device of the medical hand-grip element for injection of a medicinal substance comprises at least one rotating component that transmits a torque, e.g., a shaft, one or more gear wheels, a transmission, etc. In one embodiment, the drive device also has a motor, for example an electric motor or a motor operated with a fluid, in particular compressed air. The motor is either arranged in the medical hand-grip element or it is designed as a separate component and can be connected by a connecting device on the medical hand-grip element. The drive motor is especially preferably designed as part of a dental treatment unit, for example, a portable drive and control unit or a dental chair, so that the medical hand-grip element can be driven and can optionally be controlled for injection of a medicinal substance via this treatment unit. The control includes in particular the selection and/or adjustment of operating parameters by the user. The motor is supplied with electric power either via a power supply network or by means of a battery which, in a preferred embodiment, is arranged together with the motor in the hand-grip element, so that the hand-grip element is designed as a wireless appliance without any connection to an external unit.

The delivery device of the medical hand-grip element for injection of a medicinal substance is designed as a manually operable delivery device in one embodiment, e.g., as a rotatable or pivotable lever by means of which a rack can be moved in the direction of the ampoule. The ampoule has on one end a displaceable closure cap which is displaced directly or indirectly by the rack, so that the contents of the ampoule are forced out of it. A motor-driven delivery device is provided as an alternative with which a drive motor displaces a rack or a plunger in the direction of the ampoule.

The medical hand-grip element for injection of a medicinal substance is designed as a straight elongated hand-grip element or handpiece in one embodiment. However, the hand-grip element may of course also have other forms, e.g., it may have an angled form, in particular in the form of a pistol, or it may be designed as a contra-angle handpiece with a front section or a head section arranged at an angle.

Another disadvantage of the hand-grip element from U.S. Pat. No. 4,787,893 is that for loading the hand-grip element with the ampoule and the injection needle, the front part of the hand-grip element which holds the ampoule has to be separated from the handle part, the ampoule has to be inserted into the front part, the front part has again to be attached to the handle part and then from the outside the injection needle has to be connected to the front part of the hand-grip element and must be pushed through the rubber stopper of the ampoule. This loading operation is time-consuming and tedious for the user.

Thus another object of the present invention is to create a hand-grip element that can be loaded with the ampoule and the needle more easily.

According to one embodiment, this object is achieved by a medical hand-grip element for injection of a medicinal substance which has a preferably circular receptacle opening at one end of the hand-grip element which is designed so that the ampoule can be inserted into the hand-grip element from this end of the hand-grip element through the receptacle opening. This advantageously eliminates the need for having to disassemble the hand-grip element in loading the medical hand-grip element and in general the operation of loading the medical hand-grip element is facilitated.

In one embodiment, the receptacle device or connecting device in which the ampoule is arranged after insertion into the medical hand-grip element is completely inside the medical hand-grip element and is surrounded by an outer sleeve of the hand-grip element. Therefore in an advantageous manner a protective function for the user from the rotating ampoule is achieved.

In another embodiment, the receptacle opening is designed as part of the connecting device of the coupling arrangement. With the insertion of the ampoule through the receptacle opening, the rotationally fixed coupling of the ampoule to the injection needle is at least initiated.

Another disadvantage of the injection system described in U.S. Pat. No. 4,787,893 is that it does not offer a continuous hygiene chain and thus does not provide complete protection of the user from injuries and contamination, e.g., due to inadvertent puncturing by the used needle.

Therefore, one goal of the present invention is to create an injection system, an injection unit, an injection needle and handling procedures by which the user's risk of injury and contamination is greatly reduced.

According to one embodiment, this object is achieved by an injection system having an ampoule, an injection needle connectable to the ampoule and a locking mechanism, whereby an inseparable or single use locking mechanism is provided for locking the ampoule to the injection needle.

An inseparable locking mechanism, also referred to herein as a single use or non-releasable locking mechanism, is understood to be a locking mechanism which is designed so that a single locking or connection between the ampoule and the injection needle can be established, whereby these components are locked together, but the lock can not be released without destruction. The locking mechanism is therefore not intended and is not designed accordingly to be separated again. It follows that the locking mechanism cannot be re-used, either for previously connected components or for new components. The connection of the ampoule to the injection needle is thus inseparable for the user.

This embodiment achieves the result that after connecting the ampoule to the injection needle and thus in particular after injection of the medicinal substance into the target tissue and after contact of the injection system with the patient, the end of the cannula of the injection needle that is connected to the ampoule and protrudes through the septum into the interior space of the ampoule, for example, continues to remain in or on the ampoule. Therefore, the user is protected from injuries due to this end of the cannula.

A corresponding method for removing an ampoule and an injection needle from an injection device, e.g., from a medical hand-grip element or from a syringe rack comprises the steps:

providing an injection device having an ampoule and an injection needle, whereby the ampoule and the injection needle are connected to one another by an inseparable locking mechanism, joint removal of the ampoule and the injection needle from the injection device.

The inseparably connected ampoule and injection needle are preferably removed through a receptacle opening at one end of the hand-grip element.

In one embodiment, the locking mechanism is designed as a form-fitting mechanism or catch mechanism, whereby a part of the locking mechanism is provided on the ampoule and another part is provided on the injection needle. The part provided on the ampoule preferably comprises a setback in the outer sleeve of the ampoule, in particular the ampoule neck which is designed as a constriction in the outer sleeve. The injection needle, in particular a specially provided part of the injection needle engages in this setback in a form-fitting or locking manner.

In one embodiment, the injection needle has a cannula and a cannula apron, whereby the cannula apron has a holding section for the cannula and an adjacent connecting section for connecting the injection needle to an injection device, e.g., a medical hand-grip element or a syringe frame, and for connection to the ampoule. Preferably at least one part of the inseparable locking mechanism is provided on the connecting section of the cannula apron. Because of the small dimensions of the injection needle and the cannula apron, the design of the cannula apron as a connecting element to the injection device and as a locking mechanism with the ampoule is especially advantageous.

In one embodiment, the part of the locking mechanism provided on the injection needle comprises a form-fitting element or a catch element for engaging in the setback on the ampoule. This catch element arranged on the connecting section of the cannula apron is preferably designed as a catch nose having a contact face, which is arranged essentially at a right angle to the connecting section over its entire length. This design and an adequate length of the contact face, so that the contact face and the catch nose protrude far into the setback on the ampoule, ensure the inseparability of the locking mechanism by preventing the catch element from being pulled out of the setback.

In a preferred embodiment, the cannula apron and/or various sections, e.g., coupling elements of the cannula apron, additionally also serve as a connecting element with an injection device and/or as an antitwist protection and/or as a coupling device for the transfer of torque and/or as a chucking device for chucking the ampoule with the injection needle. The advantage of this embodiment lies in the extremely user friendly design because by connecting the injection needle to the ampoule and/or by inserting the injection needle into the injection device, several functions can be activated without the user thereby having to take additional measures or perform additional actions.

The nonreleasable locking mechanism between the ampoule and the injection needle may of course also have a different design and in particular may have a different nonreleasable locking mechanism than the form-fitting mechanism or catch mechanism described above. Thus in another embodiment, a first thread is provided on a metal cuff of the ampoule and a second thread is provided on the injection needle, whereby at least one of the two threads is plastically deformable and/or or has a plastically deformable component or is provided with a blocking element so that the threads are no longer detachable from one another after being joined.

Another approach to the problem of reducing the risk of injury and contamination for the user before and after the injection procedure consists of the fact that the injection needle has a cannula and a cannula apron, whereby the cannula has a first end for penetration into the human or animal tissue and a second end for puncturing the septum of the ampoule, the cannula apron at least partially surrounds the cannula and the cannula apron for protecting the user from unintentional injuries protrudes beyond the second end of the cannula.

Through this embodiment, the user is protected in particular from unwanted injuries due to the cannula in particular when the cannula is not connected to an ampoule, i.e., on removal of the injection needle from the package or when connecting the injection needle to the ampoule, for example.

The inside diameter of the cannula apron is preferably approximately the same size or slightly larger than the outside diameter of the ampoule at least in a section, in particular in a section in which the cannula apron protrudes above the cannula, so that the ampoule can be inserted into the cannula apron. The cannula apron thus advantageously also serves to receive, support and guide the ampoule.

An embodiment of a method for loading an injection device, in particular a medical hand-grip element for injection of a medicinal substance from an ampoule into human or animal tissue also reduces the risk of injury for the user. The method includes the steps:

providing the medical injection device,
providing an ampoule containing a medicinal substance and providing an injection needle,
connecting the ampoule to the injection needle,
inserting the ampoule into the medical injection device.

By connecting the ampoule to the injection needle before insertion into the injection device, the connection process is facilitated. Usually first the ampoule is inserted into the injection device, in particular into a medical hand-grip element, and then the injection needle is connected to the ampoule through a receptacle opening in the injection device. The receptacle openings for the injection needles are often very small so the insertion of the injection needle into this opening is difficult, which increases the risk of missing the opening and puncturing next to the opening. This is prevented by the method proposed here.

In an especially preferred embodiment of this method, an injection needle is used, which has a cannula apron which protrudes beyond the second end of the cannula, as described above. This further reduces the risk of injury to the user when connecting the ampoule to the injection needle.

In another embodiment, the ampoule is inserted through a receptacle opening on one end of the injection device, in particular on the hand-grip element, and/or the ampoule is secured with the injection needle by a coupling arrangement to prevent a relative movement.

In another embodiment, the ampoule and the injection needle connected to it are also separated from the medical injection device jointly again. This achieves the result that the end of the cannula of the injection needle, which is connected to the ampoule, remains in the ampoule even when separated from the injection device. This protects the user from injury due to this end of the cannula.

Another measure for preventing unwanted injury to the user due to the injection needles consists of creating an injection unit comprising an injection needle with a cannula and a cannula apron, a protective element that at least partially surrounds the injection needle and a connecting device, in particular a catch connection having two fixed positions, whereby one of the two positions is designed as a nonreleasable fixed position and the injection needle and the protective element are designed to be displaceable relative to one another to assume the two fixed positions.

If the injection needle is inserted into the nonreleasable fixed position, the protective element and the injection needle are no longer separable from one another. The protective element preferably surrounds that end of the cannula of the injection needle which penetrates into the tissue of the patient. After conclusion of the injection process, the injection needle, preferably still connected to the injection device, is inserted into the protective element to assume the inseparable fixed position. Then the injection needle and the protective element may be disposed of jointly and/or optionally released from the injection device jointly in advance. Due to the inseparable connection between the injection needle and the protective element, there is no risk of the user inadvertently releasing the injection needle from the protective element or becoming injured with the used injection needle either in disposal or in separating the injection device.

In an especially preferred embodiment, at least a part of the packing of the injection needle, e.g., a package container, is used as the protective element. The separable fixation position of the connecting device is the position in which the injection needle is situated before use. The user releases the injection needle before use from the package/the protective element and connects it to the ampoule and/or the injection device. After the end of the injection, the user slides the injection needle back into the package/protective element, this time selecting the inseparable fixed position. This embodiment has the advantage that a single element serves both as the package and as the protective element.

In one embodiment, the fixed positions are formed by setbacks or grooves and the connecting device comprises an engagement element, in particular a catch element for engagement in the fixed position, whereby preferably the fixed positions are provided on the protective element and the engagement element is provided on the injection needle, in particular on the cannula apron. These embodiments allow a reliable fixation in the fixed positions with at the same time good displaceability and ease of manufacture of the connecting device.

In one embodiment, the inseparability of one of the two fixed positions is achieved by an essentially rectangular edge, which is designed so that the catch element cannot be moved above it, whereas the other detachably designed fixed position has at least one steadily rising side wall, so that a catch element accommodated therein can be extracted, for example.

In another embodiment, the protective element has engagement means for a needle changer on its outside, so that removal of the injection needle from the protective element and insertion of the injection needle into the protective element can be performed with the help of a needle changer. The engagement means are designed in particular as a setback, a groove or a ring groove.

A corresponding method for disposal of an injection needle comprises the steps:
  providing an injection needle,
  providing a protective element,
  inserting the injection needle into the protective element, and
  inseparable joining of the injection needle to the protective element.

In an especially preferred embodiment, the injection needle which is inseparably connected to the protective element is connected to an ampoule at its other cannula end which is not accommodated in the protective element, in particular being connected by an inseparable locking mechanism as already described above, so that the two ends of the cannula are not exposed in disposal of the injection needle. Therefore, the risk of injury for the user in separating the injection needle from the injection device and in its disposal is further reduced.

Alternatively, in this method an injection needle which has a cannula apron as also described further above is used, said apron extending beyond the second cannula end, which is not accommodated in the protective element, thereby further reducing the risk of injury.

The invention is explained in greater detail below on the basis of preferred embodiments and with reference to the accompanying drawings:

DETAILED DESCRIPTION

Figure 1:
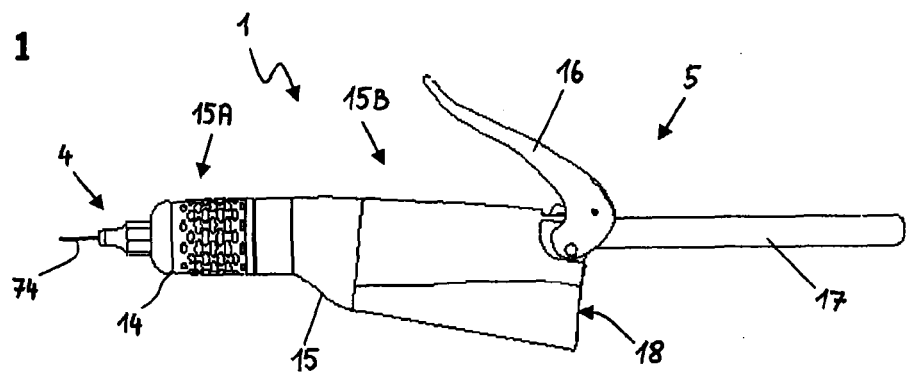
FIG. 1 shows an outside view of an embodiment of a medical hand-grip element for injection of a medicinal substance.

The embodiment of a medical hand-grip element 1 illustrated in FIG. 1 serves as a dental intraosseous handpiece, in particular for creating a borehole in a jawbone and for subsequent injection of a medicinal substance, in particular an anesthetic into the borehole and the bone. The elongated tubular hand-grip element 1 has an outer sleeve 15 with a handle section 15B and a head section 15A connected thereto. The handle section 15B and the head section 15A are joined together by a thread 27 (see FIG. 2). A receptacle opening 14, preferably circular, through which an ampoule 2 containing the anesthetic can be inserted into the hand-grip element 1 is provided at the end of the head section 15A of the hand-grip element 1. An injection needle 4 which protrudes out of the hand-grip element 1 is connected to the ampoule 2.

The injection needle 4 comprises an elongated cannula 74 which serves in a known way as a drilling instrument for cutting the borehole into the bone as well as for dispensing the anesthetic. To this end it has at least one cutting edge 86 on one end section (see FIG. 4) which, when the injection needle 4 is made to rotate, cuts bone shavings from the bone and thereby creates the borehole into the bone. The cannula 74 is additionally furnished with a cavity 87 which runs through its interior and serves as a channel for conducting the anesthetic, and an opening 88 which is connected to the cavity 87 for dispensing the anesthetic to the bone. The cannula 74 is additionally shaped so that its one end can penetrate through the rubber stopper or the septum 72 of the ampoule 2 into the interior space of the ampoule 2 containing the anesthetic.

Figure 2:
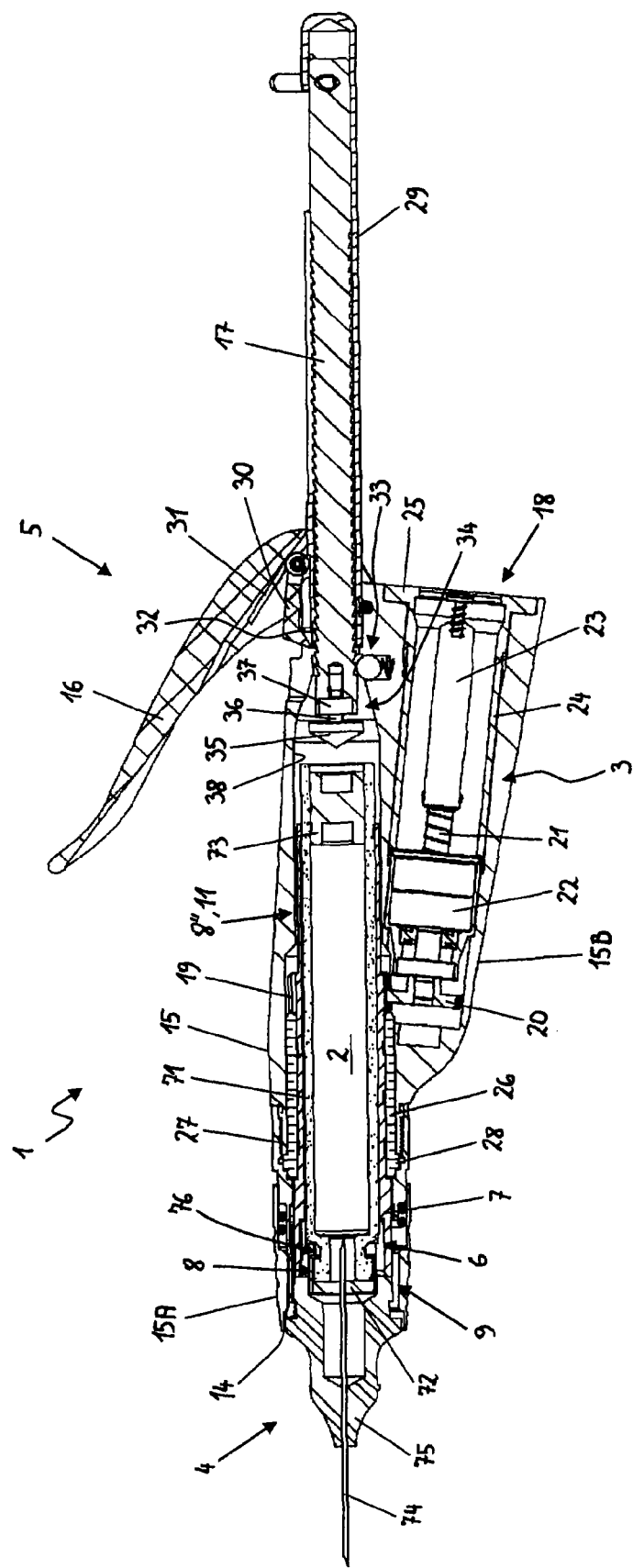
FIG. 2 shows a sectional diagram through the medical handle of FIG. 1.

To dispense the anesthetic or the medicinal substance from the ampoule 2 a delivery device 5 is provided, which, according to the embodiment in FIGS. 1 and 2, is designed as a manually operable delivery device. The delivery device 5 comprises a rotatable or pivotable lever 16, which is connected by an entraining device to a plunger or a rack 17, which is accommodated in the hand-grip element 1, so that it is displaceable in the direction of the ampoule 2, so that by displacing the rack 7 the anesthetic is delivered out of the ampoule 2 and through the cannula 74.

On the end of the hand-grip element 1 which is opposite the opening 14, a connecting device 18 is provided, serving to connect the hand-grip element 1 to a drive motor. The drive motor sets the injection needle 4 and the ampoule 2 in rotation via the drive device 3 which is arranged in the interior of the hand-grip element 1. The connecting device 18 is designed as a plug connection, a form-fitting connection or a screw connection, for example.

FIG. 2 shows an enlarged sectional diagram of the medical hand-grip element 1 of FIG. 1 with an ampoule 2 accommodated completely in the interior of the hand-grip element 1 and with an injection needle 4 that is connected to the ampoule 2 and is accommodated at least partially in the hand-grip element 1.

The ampoule 2 is inserted into a connecting member 6, which can be, e.g., a hollow shaft 7. The connecting member 6 is situated in an internal borehole 38 of the hand-grip element 1. The internal borehole 38 has two openings on its opposite ends for the delivery device 5 and for the insertion of the ampoule 2 and the injection needle 4. The opening of the internal borehole 38 for insertion of the ampoule 2 and the injection needle 4 is connected to the receptacle opening 14 of the hand-grip element 1 or is part of the receptacle opening 14.

The inside diameter of the hollow shaft 7 corresponds approximately to the outside diameter of the outer shaft 71 of the ampoule 2 so that the ampoule 2 is accommodated tightly in the hollow shaft 7. The length of the hollow shaft 7 is somewhat shorter than the length of the ampoule 2 so that the ampoule 2 protrudes out of the hollow shaft on both of its ends.

On the outside of the hollow shaft 7 a gear wheel 19 is provided which is part of the drive device 3 for rotatingly driving the ampoule 2 and the injection needle 4. The gear wheel 19 meshes with another gear wheel 20, which is pressed onto a shaft arrangement 21. The shaft arrangement 21 includes a planetary gear 22 and is connected to an entraining device 23. At least a part of the shaft arrangement 21 and the entraining device 23 are accommodated in a bearing sleeve 24 whose flange-like end 25 is part of the connecting device 18. A drive motor, e.g., a brushless electric motor can be connected to the connecting device 18, its rotational movement which is stepped down by the planetary gear 22 being transmitted to the hollow shaft 7. The rotatable hollow shaft 7 is accommodated in a bearing sleeve 26 and is slidingly supported therein. The bearing sleeve 26 is secured on a rotationally fixed component of the hand-grip element 1 via protrusions 28, e.g., on the outer sleeve 15.

Except for the gear wheel 19, the entire drive device 3 is arranged in an enlarged area of the outer sleeve 15, on the underside of the hand-grip element 1. The broadening in the outer sleeve 15 decreases in the direction of the head section 15A so that the drive device 3 is arranged obliquely, at an acute angle to the longitudinal axis of the hand-grip element 1.

The delivery device 5 comprises a manually operable pivotable lever 16 and a rack 17 which is accommodated in a protective sleeve 29. A latch 30 is provided on the lever 16 and connected to it, the front end of the latch 30 being designed with a wedge shape. The latch 30 is prestressed by a spring 31 in the direction of the rack 17. By pivoting the lever 16 alternately in the direction of the opening 14 and in the opposite direction, the rack 17 is displaced in the direction of the ampoule 2. This is accomplished by the fact that the wedge-shaped front end of the latch 30 engages between two teeth of the rack 17 through an opening 32 in the protective sleeve 29 and thereby displaces the rack 17. If the lever 16 is pivoted in the opposite direction, then the wedge-shaped front end of the latch 30 becomes detached from the rack 17 to engage back in the rack 17 with the next movement of the lever 16 in the direction of the opening 14.

A fixation device 33 which comprises a ball and a spring prestressing the ball, for example, prevents the rack 17 from slipping back in the direction of the connecting device 18 during the operation of the lever 16 and thus during the process of delivery of the anesthetic in that the ball of the fixation device 33 engages between two teeth on the rack 17.

The end of the rack 17 facing the opening 14 is designed as a rotatable shift part 34 with a wedge 35. The wedge 35 is mounted on a shaft 36 which is rotatably connected to a bearing 37. The bearing 37 is secured in a receptacle of the rack 17. If the rack 17 is moved in the direction of the opening 14, the wedge 35 engages with the displaceable sealing cap 73 of the ampoule 2 and shifts it in the direction of the septum 72 so that the substance contained in the ampoule 2 is pressed out of the ampoule 2 into the cannula 74. Since the ampoule 2 rotates during operation of the hand-grip element 1, it is necessary to support the wedge 35 rotatably so as to prevent the ampoule 2 from being braked by the rack 17 and thereby resulting in an unwanted relative movement between the ampoule 2 and the injection needle 4.

The receptacle opening 14 is of such dimensions that the injection needle 4 can be inserted together with the cannula apron 75 which at least partially surrounds the cannula 74 through the receptacle opening 14 into the into the hand-grip element 1. The injection needle 4 is connected to the hand-grip element 1 via a coupling device 8, whereby parts of the coupling device 8 are provided on the injection needle and additional coupling elements are provided on the hand-grip element 1. The coupling device 8, however, serves not only for connecting the injection needle 4 to the hand-grip element 1 but also for transferring the torque from the connecting device 6 to the injection needle 4.

Another coupling device 8" is provided on the connecting member 6 or the hollow shaft 7. The coupling device 8" comprises multiple spring straps 11 which are under tension radially toward the inside in the direction of the ampoule 2 and which secure the ampoule 2 in and on the connecting device 6. This coupling device 8" also additionally serves to transfer the torque from the connecting device 6 to the ampoule 2.

It can be seen from FIG. 2 that for the rotationally fixed connection of the ampoule 2 to the injection needle 4, the coupling arrangement 9 suppresses a relative movement between these two elements by ensuring that the torque generated by the drive device 3 is reliably transferred to the ampoule 2 and to the injection needle 4 by the coupling devices 8 and 8" and that the ampoule 2 and the injection needle 4 are connected fixedly to one another via the connecting device 6 with the hollow shaft 7. Through and jointly with the coupling device 9, the injection needle 4 and the ampoule 2 thus form a unit for transferring and/or receiving a uniform joint torque and a uniform joint rotational speed.

Figure 3:
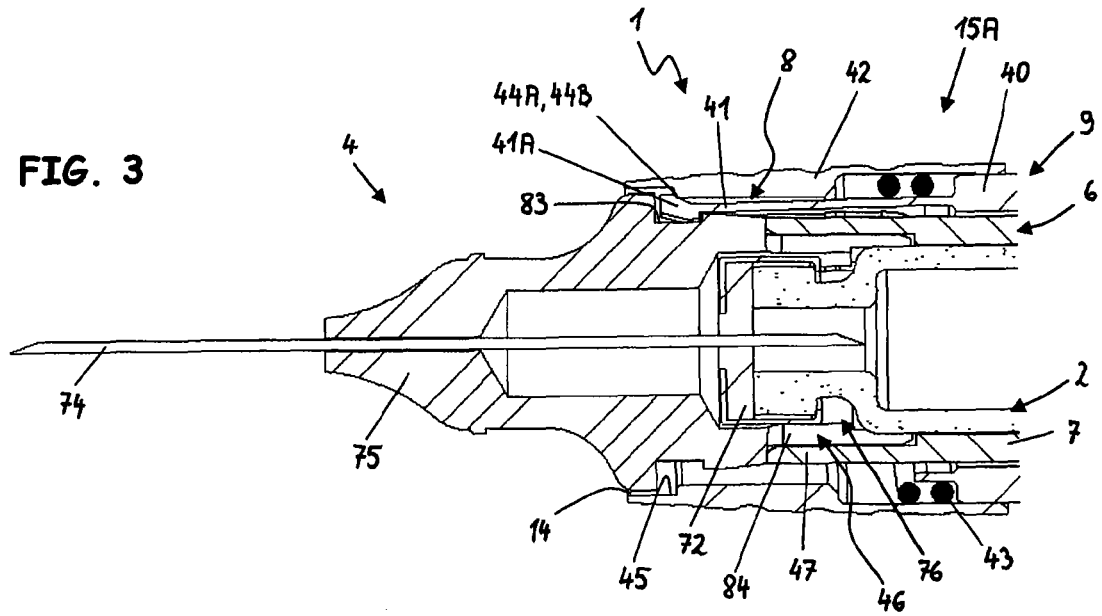
FIG. 3 shows an enlarged detail of the head section of the medical hand-grip element for injection of a medicinal substance of FIG. 2.

FIGS. 3-6 show various embodiments of the head section of medical hand-grip elements for injection of a medicinal substance from an ampoule 2, whereby FIG. 3 is an enlarged diagram of the head section 15A of the hand-grip element 1 of FIG. 2.

The coupling device 8 for fastening the injection needle 4 on the hand-grip element 1 and for transferring the torque to the injection needle 4 comprises a chucking sleeve 40 having multiple spring arms 41 on whose end catch elements 41A are provided, e.g., in the form of catch noses. As the mating coupling element, a ring groove 83 runs around the cannula apron 75 of the injection needle 4 (see also FIG. 7) with the catch elements 41A engaging into the ring groove 83, so that the injection needle 4 is secured axially on the hand-grip element 1. The spring arms 41 are surrounded by an actuator element, e.g., a shift sleeve 42, which is displaceable along the longitudinal axis of the hand-grip element 1 and is prestressed by a spring element 43 in the direction of the receptacle opening 14. Contact faces 44A, 44B provided on the shift sleeve 42 as well as on the spring arms 41 are shaped so that the catch elements 41A are pressed by the shift sleeve 42 into the ring groove 83.

If the shift sleeve 42 is pressed against the spring force of the spring 43 and moved in the direction of the delivery device 5, then the contact faces 44A, 44B are separated from one another and the catch elements 41A can yield radially outward into a setback 45 of the shift sleeve 42 so that they come out of the ring groove 83 and the injection needle 4 can be separated from the hand-grip element 1.

The components 41, 42, 43, 83, etc., of the coupling device 8 described here thus form a coupling part which serves exclusively to secure the injection needle 4 on the hand-grip element 1. According to this embodiment, the torque is transferred to the injection needle 4 via a second separate coupling part with other elements. Therefore several, preferably four, entraining elements 46, e.g., in the form of receptacles or setbacks are provided on the hollow shaft 7 and are separated from one another by separation elements 47, e.g., four webs. If the injection needle 4 is connected to the hand-grip element 1, then one or more coupling elements 84 of the injection needle 4 (see also FIG. 7), e.g., coupling noses which are part of the cannula apron 75, engage in the entraining elements 46 of the hollow shaft 7. If the hollow shaft 7 is set in rotation, then the entraining elements 46 of the hollow shaft 7 transfer the rotational movement and the torque to the coupling elements 84 and the injection needle 4.

Figure 4:
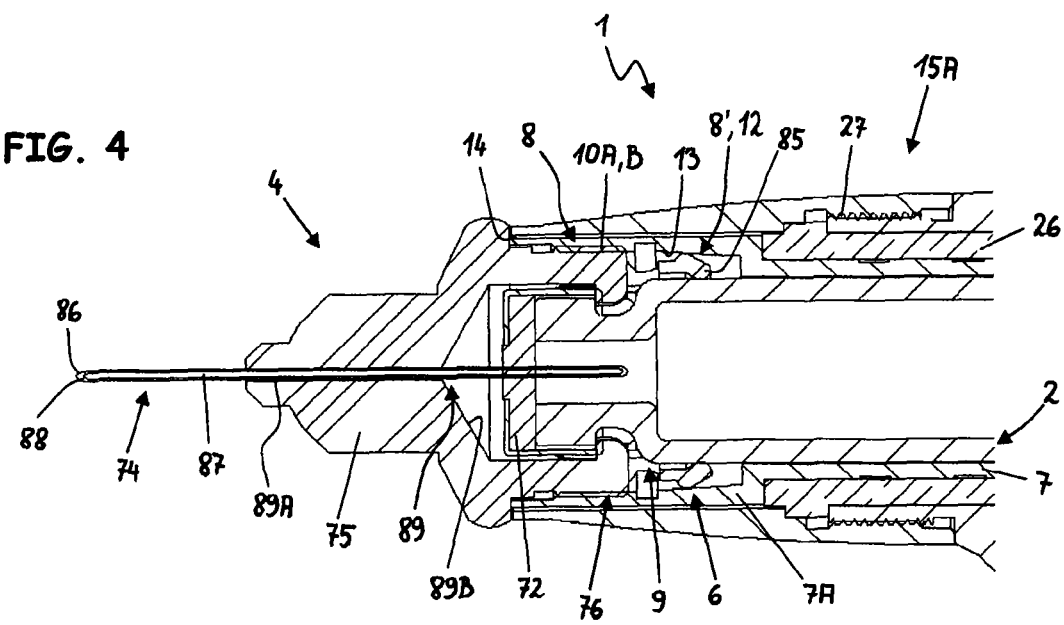
FIG. 4 shows a sectional diagram of a second embodiment of a head section of a medical handle for injection of a medicinal substance.

In contrast with that, the embodiment of the coupling device 8 illustrated in FIG. 4 is designed so that the fixation of the injection needle 4 on the hand-grip element 1 and the torque transfer to the injection needle 4 take place at the same site and through the same components. To this end, the hollow shaft 7 has a section 7A with a widened diameter on one end. An inside thread 10A which can be screwed onto the outside thread 10B of the injection needle 4, preferably of the cannula apron 75 is provided on this section 7A. If the hollow shaft 7 is set in rotation, then the rotational movement and the torque are transferred to the injection needle via the thread 10A, 10B. Instead of the threaded connection, other known connections may of course also be provided, e.g., bayonet connections, form-fitting connections with chucking straps, etc.

The coupling device 9 of FIG. 4 also has a chucking device 12 for chucking the ampoule 2 with the injection needle 4. This chucking device 12 may serve as an additional securing device for the rotationally fixed connection between the injection needle 4 and the ampoule 2; alternatively, however, it may also be provided instead of the coupling device 8'' (see FIG. 2). In this case, the torque is likewise transferred from the drive device 3 and the connecting device 6 to the ampoule 2 via the chucking device 12, so the chucking device 12 simultaneously also serves as the coupling device 8'.

The chucking device 12 includes a chucking element 13, e.g., a conical surface on the coupling arrangement 9, in particular on the widened section 7A of the hollow shaft 7. A mating chucking element 85, e.g., in the form of one or more wings is provided on the injection needle 4, in particular on the cannula apron 75. If the injection needle 4 is inserted into the hand-grip element 1 as shown in FIG. 4, then the conical surface 13 comes in contact with and presses the wing 85 radially inward in the direction of the ampoule 2. The wing 85 and the cannula apron 75 are thus pressed against the ampoule 2, thereby establishing a frictional connection between the ampoule 2 and the injection needle 4. This frictional connection serves to provide a antitwist protection and also to transfer the torque and the rotational movement to the ampoule 2.

FIGS. 2-4 also show an inseparable locking mechanism 76 for inseparable locking of the ampoule 2 to the injection needle 4, which is described further below, in particular in conjunction with FIGS. 7-9.

Figure 5:
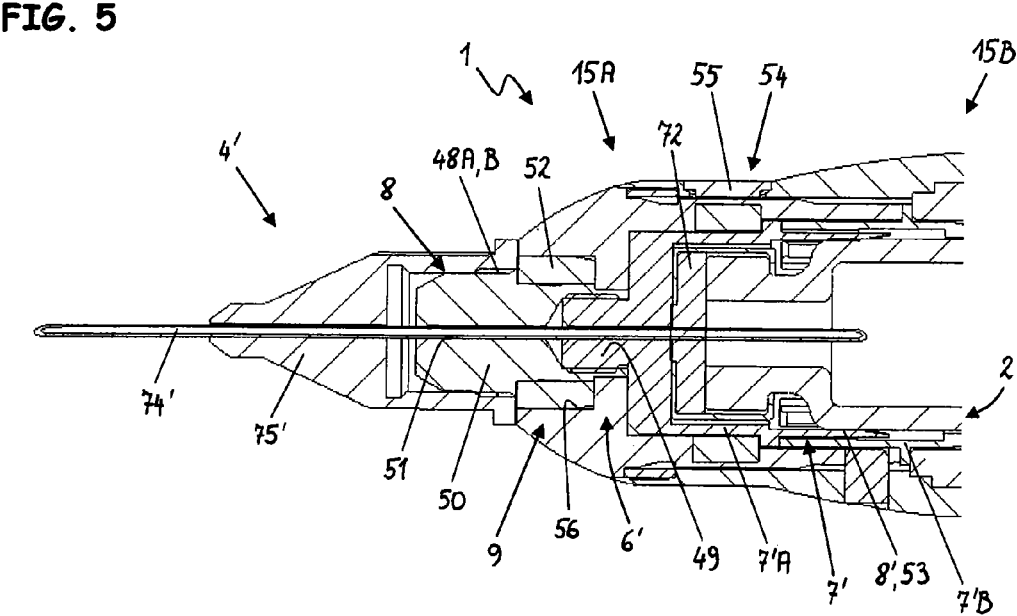
FIG. 5 shows a sectional diagram of a third embodiment of a head section of a medical handle for injection of a medicinal substance.
Figure 6:
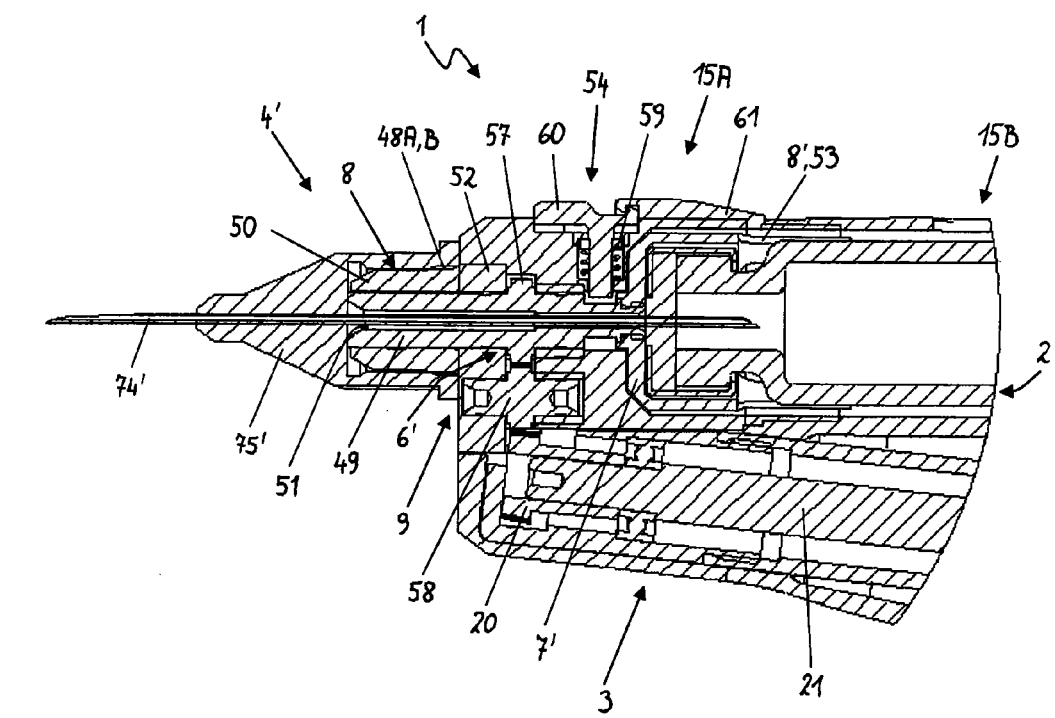
FIG. 6 shows a sectional diagram of a fourth embodiment of head section of a medical hand-grip element for injection of a medicinal substance.

FIGS. 5 and 6 show the head section 15A of a hand-grip element 15 for another type of injection needle which is provided with reference numeral 4'. This injection needle 4' is a very popular design and therefore is also referred to as a standard needle. It comprises a cannula 74' whose design is the same as that of cannula 74, and a cannula apron 75'. The cannula apron 75' is provided with an inside thread 48A which is provided for connection to a mating thread 48B on an injection device, e.g., a medical hand-grip element 1.

On the basis of the design of the injection needle 4' and the cannula apron 75', it is necessary to design the coupling arrangement 9 for rotationally fixed connection of the ampoule 2 to the injection needle 4' differently than that described for FIGS. 2-4. The coupling arrangement 9 according to FIG. 5 again comprises a connection device 6' with a hollow shaft 7'. The hollow shaft 7' is connected like the hollow shaft 7 from FIG. 2 to a gear wheel 19 to be set in rotation by the drive device 3 and it is provided with a first coupling element 8'' which secures the ampoule 2 in the hollow shaft 7' and secures the torque transfer to the ampoule 2. In contrast with the hollow shaft 7, however, the hollow shaft 7' is divided into two parts and has two separable sections 7'A, 7'B. A coupling device 8' having multiple chucking straps 53 is provided on the section 7'A, these chucking straps 53 being prestressed toward the inside, i.e., in the direction of the longitudinal axis of the hand-grip element 1 and which secure the ampoule 2 in the hollow shaft section 7'A.

The end of the hollow shaft 7' facing the injection needle 4' has a protrusion 49, which is connected to a connecting element 50, e.g., by a thread, wherein the connecting element 50 is also part of the coupling arrangement 9 and the connecting device 6'. A part of the coupling device 8 with the outside thread 48B for connecting to the injection needle 4' is provided on this connecting element 50. The connecting element 50, the protrusion 49 and the wall section of the hollow shaft 7' connected to the protrusion 49 all have a narrow borehole 51 through which the cannula 74' of the injection needle 4' is guided, so that the cannula 74' can pass through the septum 72 of the ampoule 2 into the interior of the ampoule 2, which is filled with the substance to be injected. The connecting element 50 and the protrusion 49 are rotatably mounted in the hand-grip element 1 by means of a bearing 52. The bearing 52 is accommodated in a bearing seat 56 of the head section 15A.

The transfer of the torque and the rotational movement to the injection needle 4' and the ampoule 2 is accomplished in this embodiment via the hollow shaft 7' with the coupling device 8'' (see FIG. 2) and the coupling device 8', the protrusion 49, the connecting element 50 and the coupling device 8 with the thread 48A, 48B. The rotationally fixed connection between the ampoule 2 and the injection needle 4' accomplished by the coupling device 9 is guaranteed by the rotationally fixed accommodation of the ampoule 2 in the hollow shaft 7' by the coupling device 8'' and the coupling device 8', the rotationally fixed connection of the injection needle 4' to the connecting element 50 (which is given with the threads 48A, 48B at least in the direction of rotation of the threads 48A, 48B when the threads 48A, 48B are screwed together as far as the stop) and the rotationally fixed connection of the connecting element 50 to the protrusion 49 of the hollow shaft 7'.

On the basis of the closed shaping of the hollow shaft 7' on the end facing the injection needle 4' with the protrusion 49 arranged in front of it, it is impossible with the embodiment according to FIG. 5 to shift the ampoule 2 from the front end of the hand-grip element 1 into the hollow shaft 7'. Instead of this, the hand-grip element 1 is designed in two parts so that the head section 15A can be separated from the handle section 15B of the hand-grip element 1, whereby in the separated state the hollow shaft section 7'A remains in the head section 15A and the hollow shaft section 7'B remains in the handle section 15B. After separating the two parts 15A, 15B of the hand-grip element 1, the ampoule 2 may be inserted into the hollow shaft section 7'A and then the two sections, namely the head section 15A and the handle section 15B can be joined together again, whereby the part of the ampoule 2 protruding beyond the head section 15A and the hollow shaft section 7'A is inserted into the hollow shaft section 7'B. Next the injection needle 4' can be screwed on to the connecting element 50.

The connection of the two hollow shaft sections 7'A, 7'B is accomplished by pushing them into and/or over one another. The connection of the head section 15A and the handle section 15B is accomplished by a coupling device 54. The coupling device 54 may have chucking straps prestressed toward the outside on the head section 15A, engaging in the recesses of the handle section 15B, for example. The chucking straps are brought out of engagement with the recesses by means of an elastic release mechanism 55 so that the head section 15A and the handle section 15B can be separated from one another. Other coupling mechanisms may of course also be used.

In another embodiment (not shown here), the hollow shaft is not designed to be separable but instead has a receptacle opening for the ampoule on the end facing away from the injection needle. Due to a separation of the hand-grip element as described above into a head section 15A and handle section 15B and due to the fact that the entire hollow shaft remains in the head section 15A, this receptacle opening is made accessible and the ampoule can be inserted into the hollow shaft from the rear end of the hollow shaft.

The hand-grip element 1 and the coupling device 9 according to FIG. 6 are also designed for connection of a standard needle 4'. Again a connecting element 50 is provided with a coupling device 8 having a thread 48A, 48B for connection of the injection needle 4'. The connecting element 50 is connected to a protrusion 49 on the hollow shaft 7' whereby the protrusion 49 passes completely through the connecting element 50. A bearing 52, e.g., a friction bearing, supports the connecting element 50 and the protrusion 49. A borehole 51 for the cannula 74' of the injection needle 4' passes through the protrusion 49 and the adjacent connecting wall of the hollow shaft 7'.

The hollow shaft 7' as part of the connecting device 6' is designed as a short receptacle into which only a part of the ampoule 2 can be inserted. Multiple chucking straps 53 of the coupling device 8' secure the ampoule 2 on the hollow shaft 7'.

The transfer of the rotational movement and the torque from the drive device 3 to the injection needle 4' and the ampoule 2 is accomplished according to this embodiment via the protrusion 49 which is provided with a gear wheel 57 on the hollow shaft 7', the coupling device 8' and the ampoule 2 on the one hand and on the connecting element 50, the coupling device 8" and the injection needle 4' on the other hand. An intermediate gear wheel 58 connects the gear wheel 57 that is pressed onto the shaft 21 to the gear wheel 57. The intermediate gear wheel 58 may be designed to step down the rotational speed.

The rotationally fixed connection between the ampoule 2 and the injection needle 4' accomplished by the coupling arrangement 9 is ensured by the rotationally fixed accommodation of the ampoule 2 in the hollow shaft 7' by the coupling device 8', the rotationally fixed connection of the injection needle 4' to the connecting element 50 (which in the case of the threads 48A, 48B is given at least in the direction of rotation of the threads 48A, 48B, when the threads 48A, 48B are screwed together as far as the stop) and by the rotationally fixed connection of the connecting element 50 to the protrusion 49.

Again the separation of the hand-grip element 1 into its two sections 15A, 15B is necessary for insertion of the ampoule 2 into the hollow shaft 7'. After separation, the hollow shaft 7' remains in the head section 15A so that the ampoule 2 can be inserted into the hollow shaft 7' in the direction of the protrusion 49. The locking of the head section 15A to the handle section 15B is accomplished via a coupling device 54, which has a form-fitting element 60 which is prestressed by a spring 59 on the head section 15A and has a sleeve-shaped mating element 61 which at least partially surrounds the handle section 15B and has a receptacle for engagement of a part of the form-fitting element 60. If a user presses on the form-fitting element 60 and displaces it against the spring force of the spring 59, then the form-fitting element 60 is released from the receptacle of the mating element 61 and the two sections 15A, 15B can be separated from one another.

Figure 7:
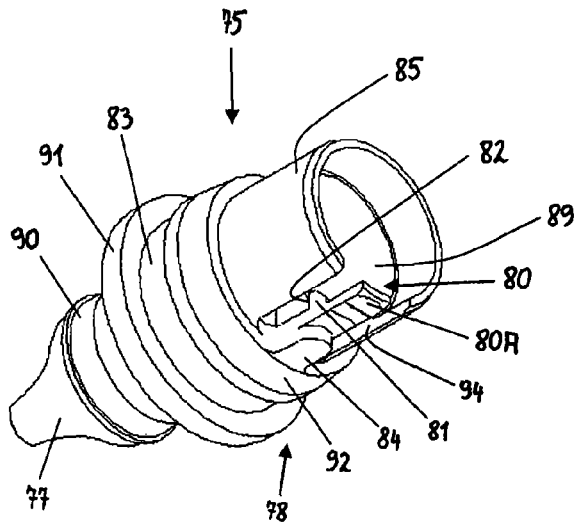
FIG. 7 shows a perspective view of an embodiment of a cannula apron of an injection needle.

FIG. 7 shows an enlarged diagram of the cannula apron 75 of the injection needle 4 from FIGS. 2-4. The cannula apron 75 has a holding section 77 and a connecting section 78 connected thereto. As can be seen from FIG. 4 in particular, a borehole 89 in which the cannula 74 is accommodated, runs through the entire cannula apron 75, whereby the borehole 89 has at least two sections 89A, 89B with different diameters. The section 89A is at least mostly arranged in the holding section 77 and the section 89B is at least mostly arranged in the connecting section 78 of the cannula apron 75. More than two sections with different diameters may of course also be provided.

The inside diameter of the borehole section 89A is approximately equal to the outside diameter of the cannula 74 at least in a sectional area, so that the cannula 74 comes in contact with the cannula apron 75 and is fixedly connected to it, e.g., is glued or cast and held in it. The diameter of the section 89B is of such a dimension at least in a sectional area that an ampoule 2 or a part of an ampoule can be inserted into this sectional area.

The holding section 77 runs generally conically toward its free forward end, and in a preferred embodiment, it has a geometric recess 90, e.g., a groove or a polygon on its other end, which faces the connecting section 78 for joining to a needle changer. A ring-shaped flange or bulge 91, which surrounds the cannula apron 75, is connected to this recess 90; in a preferred application, as explained in greater detail below, this flange or bulge 91 has a catch element or engagement element 104.

The connecting section 78, which is essentially cylindrical in shape on its outside, serves to connect the cannula apron 75 to an injection device, in particular to a hand-grip element 1, and to an ampoule 2. Connected to the bulge 91 there is a coupling element, e.g., a ring groove 83 which is provided as part of a coupling device with which the catch elements of an injection device can engage for connecting and securing the cannula apron 75 and thus an injection needle on the injection device (see also FIG. 3 and the respective description).

A ring collar 92 which preferably has a chamfer on the side facing away from the ring groove 83 is connected to the ring groove 83 so that a catch element which is to engage in the ring groove 83 can better overcome the ring collar. Several function parts extend out from the ring collar 92, at least one of these function parts being designed as an elastic component. To promote the spring effect, in a preferred embodiment, the wall thickness of at least the elastic function part is smaller than the wall thickness of the ring collar 92.

A first function part is designed as chucking element 85, e.g., as a wing, as part of a chucking device. The wing 85 is movable radially inward in the direction of the longitudinal axis of the cannula apron 75 and serves to chuck the cannula apron 75 and the injection needle 4 with the ampoule 2 (see also FIG. 4 and the respective description). Another function element is formed by the at least one coupling element 84, e.g., in the form of a coupling nose, which is part of a coupling device or entraining device for transfer of a rotational movement and a torque to the cannula apron 75 and the injection needle 4 (see also FIG. 3 and the respective description).

Another function element is part of an inseparable locking mechanism 76 for locking the ampoule 2 to the injection needle 4. The function element is preferably designed as an elongated elastic catch element 80 on which the coupling element 84 is especially preferably also arranged. A catch nose 81 with a contact face 82 for engagement in a setback on an ampoule 2 protrudes radially inward in the direction of the borehole 89 from the at least one catch element 80 (see also detailed description further below).

Figure 8:
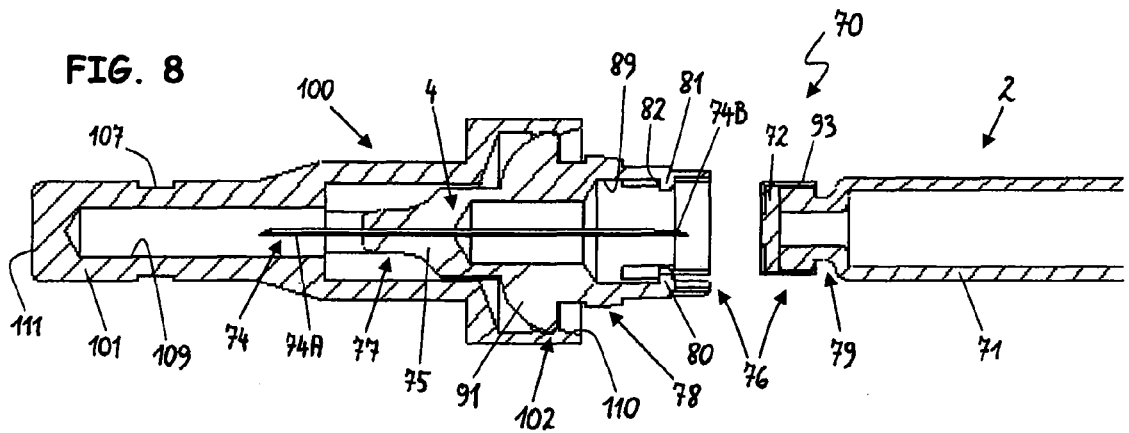
FIG. 8 shows an embodiment of an injection unit and an ampoule separate from it.
Figure 9:
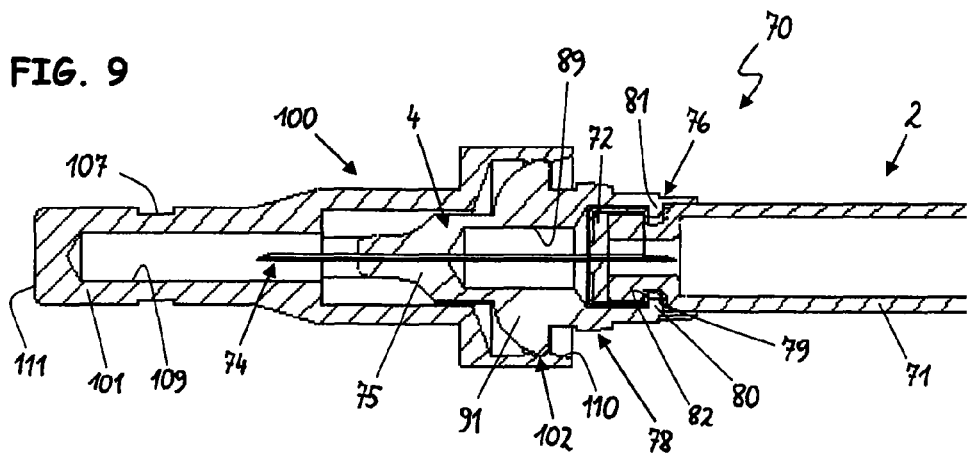
FIG. 9 shows the injection unit and the ampoule from FIG. 8 joined together.

FIGS. 8 and 9 show an injection system 70 for injection of a medicinal substance into human or animal tissue, comprising an ampoule 2 and an injection needle 4, whereby in FIG. 8 the ampoule 2 is separated from the injection needle 4 and FIG. 9 shows the ampoule 2 connected to the injection needle 4. The injection needle depicted in the two FIGS. 8 and 9 corresponds to the injection needle 4 already described with the cannula apron 75 of FIGS. 2-4 and 7. However, it is of course also possible for the injection system 70 to be equipped with an injection needle of a different design as long as this injection needle has the technical features essential for the injection system 70.

The ampoule 2 corresponds to a traditional ampoule and comprises a hollow outer sheath 71 with a first end and a second end, the septum 72 arranged on one end and a sealing cap 73 arranged on the other end, which is displaceable into the hollow outer sleeve 71. The outer sheath 71 has a constricted area or a setback 79 in the area of the end where the septum 72 is arranged. The septum 72 consists of a disk-shaped rubber sheet which is applied to one end of the outer sheath 71 and is attached thereto by a metal cuff 93. The metal cuff 93 has an opening in the center so that the cannula 74 of the injection needle 4 can penetrate through the septum 72 into the interior of the ampoule 2.

The injection system 70 has an inseparable locking mechanism 76 for locking the ampoule 2 to the injection needle 4 so that after connecting the ampoule 2 to the injection needle 4 an inseparable or single use connection is formed. As defined above, an inseparable or single use locking mechanism is understood to refer to any locking mechanism which is designed so that a single locking or connection between the ampoule 2 and the injection needle 4 can be established, whereby these components are locked together, but the lock cannot be released without being destroyed. The locking mechanism is thus not intended and not designed for being separated again. The connection of the ampoule 2 to the injection needle 4 is thus inseparable for the user.

The locking mechanism 76 is preferably designed as an inseparable catch device with at least one catch element 80 and at least one receptacle in which the catch element 80 engages, whereby especially preferably the constriction or setback 79 provided on the ampoule 2 is used as the receptacle so that no separate receptacle need be created for this. According to this, the at least one catch element 80 is arranged on the injection needle 4, preferably on the connecting section 78 of the cannula apron 75 as already mentioned in conjunction with FIG. 7. Each catch element 80 comprises an elastically designed elongated strap 80A with a free end and an end connected to the ring collar 92 and opposite the former. The at least one strap 80A is separated from the adjacent structure by two slots 94.

On its inside facing the borehole 89, the strap 80A has a catch nose 81 which is provided for engagement in the setback 79 of the ampoule 2. On its side facing the holding section 77, the catch nose 81 is provided with a contact face 82 which is arranged essentially at a right angle to the connecting section 78 over its entire length. On the opposite side, the catch nose 81 has an inclined face or a chamfer.

In connecting the ampoule 2 to the injection needle 4, the ampoule 2 is inserted into the borehole 89 of the injection needle 4 until the catch noses 81 come in contact with the metal cuff 93 of the ampoule 2 on their chamfered sides. Because of the elastic design of the straps 80A, the catch elements 80 bend radially outward so that the catch noses 81 slide with their chamfered sides over the metal cuff 93 until they engage in the setback 79 of the ampoule 2 (see FIG. 9). The design of the catch noses 81, in particular the contact faces 82, which run at a right angle to the connecting section 78 in particular and come in contact with a mating face of the setback 79, and the length of the catch noses 81 produce such a tight connection that it is impossible to separate the injection needle 4 from the ampoule 3, e.g., by pulling the ampoule 2 and the injection needle 4 apart axially. The ampoule 2 and the injection needle 4 thus remain permanently locked together after they have been joined so that the risk of injury for the user is reduced because the end 74B of the cannula 74 is permanently accommodated in the ampoule 2.

FIG. 8 also shows that injection needle 4 has another safety feature for protecting the user from unwanted injuries. The cannula 74 of the injection needle 4 has a first end 74A for penetrating into human or animal tissue and a second end 74B for puncturing the septum 72 of the ampoule 2, whereby the cannula apron 75 at least partially surrounds the cannula 74 and whereby the cannula apron 75 protrudes beyond the second end 74B of the cannula 74 to protect the user from unwanted injuries. The cannula apron 75 preferably protrudes beyond the cannula 74 by a few millimeters, especially preferably approximately 2-5 millimeters. Through this measure the risk of unwanted puncturing in connecting the injection needle 4 to the ampoule 2 or an injection device is reduced in particular.

Figure 11:
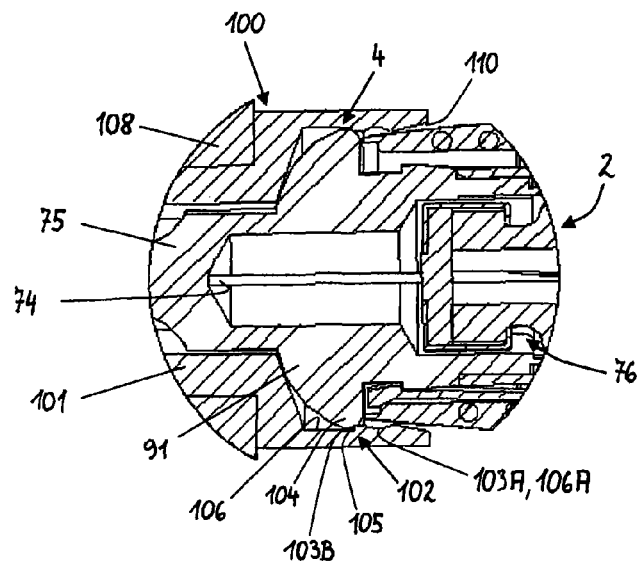
FIG. 11 shows an enlarged detail view of an embodiment of a connecting device in an injection needle for connecting an injection needle to a protective element.

FIGS. 8, 9 and 11 also show an injection unit 100 which comprises an injection needle 4 with a cannula 74 and a cannula apron 75 and a protective element 101 which at least partially surrounds the injection needle 4. In addition, a connecting device 102, in particular a catch connection having two fixed positions 103A, 103B is provided, whereby one of the two fixed positions is designed as an inseparable fixed position 103B and whereby the injection needle 4 and the protective element 101 are designed displaceably in relation to one another to assume the two fixed positions 103A, 103B.

The injection needle shown here corresponds to the injection needle 4 already described having the cannula apron 75 of FIGS. 2-4 and 7, but it should be pointed out that it is possible to equip the injection unit 100 with an injection needle of a different design as long as this injection needle has the technical features essential for the injection unit 100.

The protective element 101 is an elongated element preferably made of plastic and having an internal borehole 109, into which the at least one part of the injection needle 4 can be inserted. The internal borehole 109 has multiple sections with different inside diameters so that different sections of the injection needle 4, e.g., the holding section 77 and the connecting section 78 can be accommodated in these sections. The sections having the different inside diameters are separated from one another by ring shoulders or steps. The protective element 101 additionally has a closed end 111 with a continuous transverse wall and an open end with an opening 110 for inserting the injection needle 4. On the outside circumference of the protective element 101, engagement means 107 for a needle changer 108 are provided, e.g., one or more setbacks or a groove. In a preferred embodiment at least a portion of the packaging of the injection needle is used as the protective element 101, in particular that part of the packaging which surrounds the end of the cannula 74 which is provided with the cutting edge 96.

The connecting device 102 comprises parts on the protective element 101 and parts on the injection needle 4. The fixed positions 103A, 103B which are formed in particular by setbacks or grooves 106A, 106B are preferably provided on the inside of the protective element 101, whereas the engagement element 104 for engaging in the fixed positions 103A, 103B, in particular a catch element, is provided on the injection needle 4, in particular on the cannula apron 75 (see FIG. 11). The engagement element 104 is formed by the flange or bulge 91 or by a section thereof, in particular by an edge on the flange 91.

The two fixed positions 103A, 103B are arranged side-by-side and/or in series one after the other, so that the engagement element 104 can engage in only one of the two fixed positions 103A, 103B. The inseparability of the fixed position 103B is achieved in one embodiment by an edge 105 arranged essentially at a right angle with respect to the inside wall of the borehole 109. In contrast with that, the other detachably designed fixed position 103A has at least one steadily ascending side wall. An inseparable fixed position is understood to refer to any fixed position designed so that a unique locking or connection can be established between the injection needle 4 and the inseparable fixed position, whereby the connection can no longer be released without destroying it. Therefore, this connection is not intended or designed to be separated again. The connection of the injection needle 4 to the protective element 101 is thus inseparable for the user.

The connecting device 102 allows the protective element 101 to be used in a double function, namely first as a storage and/or delivery and/or packaging container in which the sterile unused injection needle 4 is stored, for example, while on the other hand it serves as a protective container after conclusion of use of the injection needle 4, whereby after completion of use, it is to be guaranteed that the used injection needle 4 is not inadvertently used again or that the protective container becomes detached from the used injection needle and there is a risk that a user might be injured on the uncovered cannula tip.

This is achieved by the connecting device 102 with the two fixation positions 103A, 103B. If the protective element 101 serves to store the injection needle 4, then the engagement element 104 is in the releasable position 103A (see FIG. 9) to which the injection needle 4 can also be brought repeatedly and released again. For use of the injection needle 4, it is pulled out of the protective element 101 and the connecting device 102 through the opening 110. If the use of the injection needle 4 is terminated and if the injection needle 4 is to be disposed of, then the engagement element 104 is brought into engagement with the inseparable fixed position 103B. This is accomplished by inserting the injection needle 4 through the opening 110 into the protective element 101, whereby the engagement element 104 first engages in the releasable fixed position 103A which is closer to the opening 110. If the user inserts the injection needle 4 further into the borehole 109 of the protective element 101 in the direction of the closed end 111, then the engagement element 104 slides over the steadily rising side wall of the releasable fixed position 103A, overcomes the edge 105 arranged at a right angle and engages in the nonreleasable fixed position 103B (see FIG. 11). Then the injection needle 4 can be disposed of together with the protective element 101 without there being a risk that the protective element 101 will become detached from injection needle and cause injuries.

Figure 12:
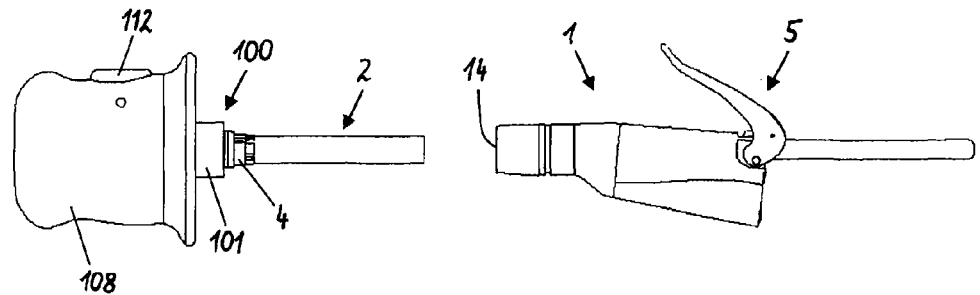
FIG. 12 shows an embodiment of a needle holder and an injection unit connected to it as well as a medical hand-grip element into which the injection unit can be inserted.

In a preferred embodiment, the injection needle 4 remains connected with the ampoule 2 even after engagement in the nonreleasable fixed position 103B, so that the two ends 74A, 74B of the cannula 74 are covered so this further reduces the risk of injury. This situation is depicted in FIG. 12 where a needle changer 108 is used, as described in greater detail below, for the handling of the protective element 101, so that the protective element 101 is now largely accommodated in the needle changer 108. The injection needle 4, the ampoule 2 and the protective element 101 form a unit which is attached to the needle changer 108 and which is separated from the injection device, e.g., a medical hand-grip element 1. By activation of the pushbutton 112, the injection needle 4, the ampoule 2 and the protective element 101 can be released from the needle changer 108 and discarded.

Figure 10:
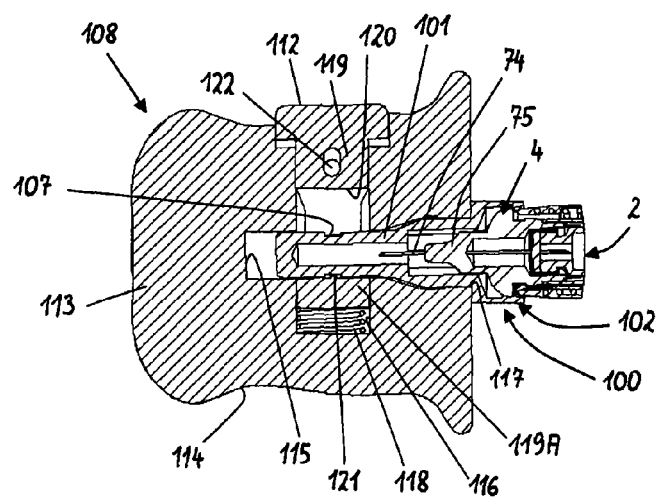
FIG. 10 shows an embodiment of a needle changer with an injection unit clamped in it.

FIG. 10 shows a needle changer 108 which facilitates the removal of the injection needle 4 from the protective element 101 and its insertion into the protective element 101. The needle changer 108 comprises a body 113 which is preferably ergonomically shaped. In particular the needle changer 108 has one or more recesses 114 on its outside circumference, e.g., setbacks, notches, grooves, strips or guides for engagement and for improved positioning of the user's hand.

Two angled boreholes 115, 116, preferably arranged approximately at a right angle to one another, are arranged in the body 113 of the needle changer 108. The borehole 115 is provided to receive the protective element 101 through the opening 117 and is adapted in its shape to the external shape of the protective element 110. For example, it has several sections with different inside diameters. A spring element 118, in particular a spiral spring, a shift element 119 with a borehole 120, e.g., a displaceable shaft and a pushbutton 112 connected to the shift element 119 or some other actuating element are provided in the borehole 116. The pushbutton 112 is arranged in a recess in the borehole 116 with an enlarged inside diameter and protrudes beyond the borehole 116 with its free end so that it is readily accessible for the user and is easy to operate. The shift element 119 is secured in the needle changer 108 by a pin 122 which is guided in an elongated hole in the shift element 119.

If no protective element 101 is inserted into the needle changer 108, then the spring element 118 pushes the shift element 119 in the direction of the pushbutton 112 so that a portion 119A of the shift element 119 which is arranged between the borehole 120 and the spring element 118 is situated in the borehole 115. If a protective element 101 is inserted into the borehole 115, the protective element 101 displaces the part 119A against the force of the spring element 118 in the direction of the spring element 118 so that at least a portion of the borehole 120 of the shift element 119 is aligned with the borehole 115 and the protective element 101 can be shifted through the borehole 120 in the direction of the closed end of the borehole 115. A catch element 121, e.g., a catch nose, which engages in the engaging means 107 of the protective element 101 is provided on the part 119A of the shift element 119. The protective element 101 is secured in the needle changer 108 due to the catch element 121 and the spring force of the spring element 118, which presses the protective element 101 against the inside wall of the borehole 115, so that the injection needle 4 can be removed from the protective element 101 or can be inserted into it.

The release of the protective element 101 is accomplished by pressing on the pushbutton 112 so that the shift element 119 is shifted against the force of the spring element 118 in the direction of the spring element 118 and releases the protective element 101. If the protective element 101 is used as packaging and for disposal of the injection needle 4, then the protective element 101 can remain in the needle holder 101 during the use of the injection needle 4.

A method for handling an injection needle and for loading and unloading an injection device, in particular a medical hand-grip element 1, is described below. This method is designed so that the risk of injury of the user with the injection needle 4 and unintentional puncturing is greatly reduced. This method consists of a plurality of individual steps, some of which can be combined into separate sub-methods. The use of a single step or one or more of these sub-variants, some of which were already described in the description of FIGS. 1-12, also reduces the risk of injury for the user at least in a partial step of handling of an injection needle or an injection device. The greatest protection in the form of a continuous closed hygiene chain, however, is achieved by using the overall method described below.

The starting point for this method is an unused injection needle, usually sterile, which is accommodated in a package, e.g., a packaging container. The injection needle is preferably designed as injection needle 4 according to FIGS. 2-4 and 7-9. The package container is designed in two or more parts and comprises the protective element 101. The injection needle 4 is a accommodated in the protective element 101 and is in the releasable fixed position 103A.

In a first step, the packaging container is opened and all the parts of the packaging container except for the protective element 101 are removed from the injection needle 104. These packaging parts may be disposed of because they will not be needed further. Thus the user has an injection unit 100 comprising the injection needle 4 and the protective element 101 as illustrated in FIG. 8. The two ends 74A, 74B of the cannula 74 are covered by the protective element 101 and by the cannula apron 75 protruding beyond the end of the cannula 74B, respectively, so that the user is protected from unintentional puncturing by the cannula.

In the next step, the user attaches the injection unit 100 to the ampoule 2 by inserting the ampoule 2 into the cannula apron 75, whereby at the same time the cannula 74 punctures through the septum 72 and penetrates into the interior of the ampoule 2, which is filled with the substance to be injected. The cannula apron 75 here is designed so that the ampoule is centered with respect to the cannula even on insertion. In addition, a nonreleasable locking mechanism 76 is preferably also provided, so that the ampoule 2 and the injection needle 4 are inseparably joined together. The situation after joining the ampoule 2 to the injection unit 100 is illustrated in FIG. 9. As also explained below, the ampoule 2 remains connected to the injection needle 4 during the entire remaining procedures including disposal so that the cannula end 74B is covered by the ampoule 2 and there is no risk for the user of being injured with this cannula end 74B.

In the next step, the injection unit 100, which is now connected together with the ampoule 2, is connected to the injection device, in particular to a medical hand-grip element 1. If a medical hand-grip element 1 is used, the connection is accomplished preferably by insertion of the ampoule 2 and the injection needle 4 through a receptacle opening 14 on one end of the hand-grip element 1, as described already above. Through the connection to a medical hand-grip element 1, a coupling between the ampoule 2 and/or the injection needle 4 and a coupling element 10, 11 for transfer of a driving movement and a torque and/or a chucking between the ampoule 2 and the injection needle 4 by a chucking device and/or a coupling of the ampoule 2 to the injection needle 4 for a rotationally fixed connection of the two elements by a coupling device 9, as also explained in detail above preferably also take place at the same time.

Next, the protective element 101 is removed from the injection needle 4, whereby a needle changer 108 as described above is preferably used for this purpose. The protective element 101 especially preferably remains in the needle changer 108. The injection device is then ready to be used for injection of the medicinal substance. This is shown in FIG. 1 on the example of a medical hand-grip element 1.

After conclusion of use of the injection needle 4, it is inserted into the protective element 101, whereby as described above, the injection needle 4 is pushed into the nonreleasable fixed position 103B so that a nonreleasable connection is formed between the injection needle 4 and the protective element 101 (see FIG. 11). As already mentioned, the protective element 101 is preferably part of the packaging of the injection needle and especially preferably is secured in the needle changer 108, but it is also possible to use a separate protective element 101 that is not used as the packaging for the unused injection needle 4 and/or to perform the insertion of the injection needle 4 into the protective element 101 without a needle changer 108.

In the next step, the ampoule 2, the injection needle 4 and the protective element 101 are separated from the injection device, in particular from the medical handpiece 1, as illustrated in FIG. 12.

Then the ampoule 2, the injection needle 4 and the protective element 101 are discarded jointly as a unit, preferably being inseparably joined together by the locking mechanism 76 and by the connecting device 102.

As indicated by the description of the method and the construction of the injection needle 4, the injection system 70 and the injection unit 100, both ends 74A, 74B of the cannula 74 are covered during the entire procedure—except the use of the needle immediately before, during and after the injection—so the user is provided with maximum protection from injuries.

The embodiments described herein are not limiting in any way, but instead are illustrative of all embodiments that use or include the basic logical or functional principles. In particular the injection systems, injection units, injection needles and handling methods described herein can be used not only in combination with the medical hand-grip element described here but may also be used with all other injection devices, e.g., as part of syringes or with syringe racks.

Additionally all the different embodiments described here may also be combined with one another, and several or all of the methods described here may be executed simultaneously or in succession as part of an overall process, the devices described here may be used in these methods or in individual method steps and/or the methods may be performed with the devices described.

What is claimed is:

1. A medical hand-grip element for injection of a medicinal substance from an ampoule through an injection needle into human or animal tissue, the medical hand-grip element comprising:
   a housing, a drive device for rotatingly driving an ampoule and an injection needle relative to the housing, a delivery device configured for selective delivery of a medicinal substance from the ampoule and an antitwist coupling arrangement positioned at least partially within the housing and configured to maintain substantially the same rotational speed for the ampoule and for the injection needle relative to the housing,
   wherein the antitwist coupling arrangement comprises a connecting member arranged at least partially within the housing, wherein the connecting member comprises a hollow shaft which is configured to surround and accommodate within its interior at least a portion of the ampoule and to connect to the injection needle,
   wherein the hollow shaft of the connecting member comprises a gear wheel to connect to the drive device for rotatingly driving the ampoule and the injection needle,
   wherein the antitwist coupling arrangement comprises a first coupling element for transferring torque to the injection needle and a second coupling element to transfer torque from the connecting member to the ampoule, said first and second coupling elements being arranged at the hollow shaft of the connecting member, and
   wherein the antitwist coupling arrangement is configured to form a unit with the ampoule and the injection needle on which essentially the same torque acts and which thus rotates at essentially the same rotational speed, so that relative movement between the ampoule and the injection needle is substantially prevented.

2. The medical hand-grip element according to claim 1, wherein the first coupling element comprises at least one of a spring strap, a spring arm, a chucking face, a thread, an entraining element and a form-fitting element and wherein the second coupling element comprises at least one of a spring strap, a spring arm, a chucking face, a thread, an entraining element and a form-fitting element.

3. The medical hand-grip element according to claim 1, wherein
   the connecting member is elongated and the hollow shaft comprises a borehole defined therein to accommodate the ampoule and wherein the second coupling element comprises spring straps which are under tension radially toward the inside of the borehole to secure the ampoule and to transfer torque to the ampoule.

4. The medical hand-grip element according to claim 1, wherein
   the coupling arrangement comprises a chucking device configured for chucking the ampoule with the injection needle.

5. The medical hand-grip element according to claim 4, wherein
   the chucking device comprises at least one conical surface.

6. The medical hand-grip element according to claim 1, wherein
   the coupling arrangement comprises a chucking device configured for chucking the ampoule with the injection needle, and wherein the chucking device is also configured as a coupling element to transfer torque to the ampoule and/or the injection needle.

7. The medical hand-grip element according to claim 1, comprising
   a receptacle opening defined at a first end of the hand-grip element, the receptacle opening being sized to receive the ampoule when the ampoule is inserted into the receptacle opening from the first end.

8. The medical hand-grip element according to claim 7, wherein
   the receptacle opening is defined in the connecting member.

9. The medical hand-grip element according to claim 1, further comprising an ampoule and an injection needle connectable to the ampoule to form an assembly, wherein the ampoule comprises a hollow outer sheath with first and second ends, a septum arranged at the first end and a closing cap provided on the second end, the closing cap being displaceable within the hollow sleeve from the second end in a direction towards the first end, the injection needle comprising a cannula and a cannula apron, and wherein the ampoule and the injection needle comprise a single use locking mechanism configured to lock the ampoule to the injection needle and to prevent unlocking of the ampoule from the injection needle, wherein the ampoule and the injection needle when assembled together are removable from the injection system as a single assembly.

10. The medical hand-grip element according to claim 9, wherein
    the cannula apron comprises a holding section within which the cannula is received and a connecting section shaped to connect the injection needle to an injection device and to the ampoule.

11. The medical hand-grip element according to claim 10, wherein
    at least a portion of the single use locking mechanism for locking the ampoule to the injection needle is provided on the connecting section of the cannula apron.

12. The medical hand-grip element according to claim 10, wherein
    the connecting section of the cannula apron comprises at least one coupling element for connection of the injection needle to an injection device.

13. The medical hand-grip element of claim 12, wherein the at least one coupling element comprises a ring groove formed on the cannula apron.

14. The medical hand-grip element according to claim 10, wherein
    the connecting section of the cannula apron has at least one part of an antitwist protection and/or a coupling device for torque transfer and/or a part of a chucking device for chucking the ampoule with the injection needle.

15. The medical hand-grip element of claim 14, wherein the connecting section of the cannula apron comprises a coupling nose.

16. The medical hand-grip element according claim 9, wherein
    the locking mechanism comprises a setback and at least one catch element engageable in the setback.

17. The medical hand-grip element according to claim 16, wherein
    the setback is positioned on the ampoule
    the at least one catch element is arranged on the connecting section of the cannula apron and comprises a catch nose for engagement in the setback, wherein the catch nose comprises a contact surface configured to contact the setback and to couple the ampoule to the injection needle when the cannula and the injection needle are secured together.

18. The medical hand-grip element according to claim 9, wherein
the cannula comprises a first end for penetration into the human or animal tissue and a second end for puncturing through the septum of the ampoule, and wherein the cannula apron at least partially surrounds the cannula and protrudes beyond the second end of the cannula to protect the user from unintentional injuries.

19. A method of using the medical hand-grip element of claim 1 to inject a medicinal substance from the ampoule into human or animal tissue.

20. The method according to claim 19, further comprising inserting the ampoule through a receptacle opening at one end of the medical hand-grip element.

21. The method according to claim 19, further comprising an ampoule and an injection needle, wherein the ampoule comprises a hollow outer sheath with first and second ends, a septum arranged at the first end and a closing cap provided on the second end, the closing cap being displaceable within the hollow sleeve from the second end in a direction towards the first end, the injection needle comprising a cannula and a cannula apron, and wherein the ampoule and the injection needle comprise a single use locking mechanism, the method further comprising connecting the ampoule and the injection needle together to form an assembly and configuring the single use locking mechanism to lock the ampoule to the injection needle and to prevent unlocking of the ampoule from the injection needle.

22. The method according to claim 21, further comprising:
removing the ampoule and the injection needle connected to the ampoule from the medical hand-grip element without separating the ampoule from the injection needle.

* * * * *